US010821190B2

(12) United States Patent
Yang et al.

(10) Patent No.: US 10,821,190 B2
(45) Date of Patent: Nov. 3, 2020

(54) HIV PEPTIDE VAULTS AND METHODS OF MAKING AND USING THEREOF

(71) Applicant: The Regents of the University of California, Oakland, CA (US)

(72) Inventors: Otto O. Yang, Los Angeles, CA (US); Leonard H. Rome, Tarzana, CA (US); Jan Mrazek, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 74 days.

(21) Appl. No.: 16/097,248

(22) PCT Filed: May 1, 2017

(86) PCT No.: PCT/US2017/030442
§ 371 (c)(1),
(2) Date: Oct. 27, 2018

(87) PCT Pub. No.: WO2017/192459
PCT Pub. Date: Nov. 9, 2017

(65) Prior Publication Data

US 2019/0111146 A1 Apr. 18, 2019

Related U.S. Application Data

(60) Provisional application No. 62/330,609, filed on May 2, 2016.

(51) Int. Cl.

| | |
|---|---|
| ***A61K 39/00*** | (2006.01) |
| ***C07K 14/00*** | (2006.01) |
| ***C07K 14/47*** | (2006.01) |
| ***C07K 16/28*** | (2006.01) |
| ***G01N 33/569*** | (2006.01) |
| ***A61K 47/64*** | (2017.01) |
| ***A61K 47/69*** | (2017.01) |
| ***A61P 31/18*** | (2006.01) |
| ***C07K 14/16*** | (2006.01) |

(52) U.S. Cl.
CPC ........ *A61K 47/646* (2017.08); *A61K 47/6901* (2017.08); *A61P 31/18* (2018.01); *C07K 14/16* (2013.01); *C07K 14/47* (2013.01); *C07K 2319/00* (2013.01); *C07K 2319/735* (2013.01); *C12N 2740/16022* (2013.01); *C12N 2740/16122* (2013.01); *C12N 2740/16222* (2013.01); *C12N 2740/16322* (2013.01)

(58) Field of Classification Search
CPC ....... C07K 2319/00; C07K 7/06; A61P 35/00; A61P 35/02; A61K 38/00
See application file for complete search history.

(56) References Cited

U.S. PATENT DOCUMENTS

| | | | |
|---|---|---|---|
| 2005/0175627 | A1 | 8/2005 | Schneider |
| 2016/0008452 | A1 | 1/2016 | Kickhoefer et al. |

OTHER PUBLICATIONS

Putorti et al., "A vaulted mystery", The Scientist Magazine, 2014:1-8.*
International Search Report received in PCT/US2017/030442 dated Aug. 3, 2017.
Putorti, et al., "A Vaulted Mystery", Aug. 1, 2014, pp. 19, Publisher: The Scientist Magazine.
Written Opinion received in PCT/US2017/030442 dated Aug. 3, 2017.

* cited by examiner

*Primary Examiner* — Barry A Chestnut
(74) *Attorney, Agent, or Firm* — Suzannah K. Sundby, Esq.; Canady + Lortz LLP

(57) ABSTRACT

Disclosed herein are compositions comprising HIV peptide vaults, which are vault particles comprising complexes of MVP proteins and one or more HIV peptides bound or genetically linked to one or more MVP proteins or packaged within the internal cavities of the vault particles and methods of using thereof.

14 Claims, 8 Drawing Sheets

Specification includes a Sequence Listing.

Conserved Region GAG1 148-214 (cGag-1):

```
             148        158        168        178        188        198        208
CladeB       SPRTLNAWVK VVEEKAFSPE VIPMFSALSE GATPQDLNTM LNTVGGHQAA MQMLKETINE EAAEWDR
Mosaic seq1  T--------- ---------- -----T---- ----S----- ---I------ -----D---- -------
Mosaic seq2  -A-------- -----G-N-- ---------- ---------- ---------- ---------- -------
Mosaic seq3  ---------- -I-------- --------A- --------M- --I------- -----D---D -------
```

Conserved Region GAG2 250-335 (cGag-2):

```
             250        260        270        280        290        300        310        320        330
CladeB       NPPIPVGEIY KRWIILGLNK IVRMYSPTSI LDIRQGPKEP FRDYVDRFYK TLRAEQASQE VKNWMTETLL VQNANPDCKT ILKALG
Mosaic seq1  -------D-- --------D- ---------- ---------- --------F- V------T-D ------D--- ---------- --R---
Mosaic seq2  ---V------ ----V----- -------V-- ---------S ---------- ---------D ---------- ---S------ ------
Mosaic seq3  ---------- ---------- -------V-- ---K------ --------F- -------T-- ---------- ---------S ------
```

Conserved Region ENV 521-606 (cEnv):

```
             521        531        541        551        561        571        581        591        601
CladeB       GFLGAAGSTM GAASMTLTVQ ARQLLSGIVQ QQNNLLRAIE AQQHLLQLTV WGIKQLQARV LAVERYLKDQ QLLGIWGCSG KLICTT
Mosaic seq1  ----V----- ----I----- ---------- --S------- ------K--- -------T-- --I------- ----L----- ----P-
Mosaic seq2  ----T----- ----L----- ---V------ ---------- ----M----- ---------- ---------- ---------- -I----
Mosaic seq3  ---------- ---------- --L------- --S---K--- ---------- ---------I -------R-- ---------- ------
```

Conserved Region NEF 106-148 (cNef):

```
             106        116        126        136        146
CladeB       RQDILDLWVY HTQGYFPDWQ NYTPGPGIRY PLTFGWCFKL VPV
Mosaic seq1  --E------- ----F----- ---------- -------Y-- ---
Mosaic seq2  -K-------- N--------H -------T-F ---------- ---
Mosaic seq3  ---------- ---------- -------V-- --------E- ---
```

HIV PEPTIDE VAULTS AND METHODS OF MAKING AND USING THEREOF

ACKNOWLEDGEMENT OF GOVERNMENT SUPPORT

This invention was made with Government support under Grant Number AI106528, awarded by the National Institutes of Health. The Government has certain rights in the invention.

REFERENCE TO A SEQUENCE LISTING SUBMITTED VIA EFS-WEB

The content of the ASCII text file of the sequence listing named "20160429_034044_164P1_seq ST25" which is 11.3 kb in size was created on Apr. 25, 2016, and electronically submitted via EFS-Web herewith the application is incorporated herein by reference in its entirety.

BACKGROUND OF THE INVENTION

1. Field of the Invention

The present invention relates to vaccines against human immunodeficiency virus.

2. Description of the Related Art

To date, vaccine designs to elicit CTL responses (predominately other viruses modified as vectors to deliver HIV-1 protein genes) have failed in human trials. They have either been weakly immunogenic for CTLs (e.g., canarypox vectors) or otherwise modestly immunogenic for responses that fail to prevent infection or reduce viremia in people who got infected after vaccination (e.g., recombinant adenovirus-5 vectors). To date, all of the HIV-1 vaccine designs that have advanced to human efficacy trials have failed. At least four problems explain these failures: 1) interference with developing immune responses against the delivered HIV-1 antigens due to competition by immune responses against the vector, 2) poorly efficient delivery of HIV-1 antigens, 3) inability to generate CTL responses at the mucosal surfaces where HIV-1 transmission occurs, and 4) mutational escape of HIV-1 from the CTL responses generated by the vaccine.

Thus, a need still exists for effective vaccines against HIV-1.

SUMMARY OF THE INVENTION

In some embodiments, the present invention provides an HIV peptide vault which comprises a vault particle comprising a complex of MVP proteins and at least one HIV peptide bound or genetically linked to at least one MVP protein or packaged within an internal cavity of the vault particle. In some embodiments, the at least one HIV peptide is an HIV epitope and/or has a sequence that is a consensus sequence, an ancestral sequence, or a mosaic sequence. In some embodiments, the at least one HIV peptide is a conserved region of a human immunodeficiency virus. In some embodiments, the at least one HIV peptide is a conserved region of Gag, a conserved region of Env, or a conserved region of Nef of a human immunodeficiency virus. In some embodiments, the at least one HIV peptide is a consensus sequence, an ancestral sequence, or a mosaic sequence of a conserved region of a human immunodeficiency virus, such as a conserved region of Gag, a conserved region of Env, or a conserved region of Nef of a human immunodeficiency virus. In some embodiments, an HIV peptide vault comprises two or more different HIV peptides. In some embodiments, the HIV peptide comprises a sequence having at least 90%, at least 95%, at least 96%, at least 97%, at least 98%, or at least 99% sequence identity to a sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16. In some embodiments, the HIV peptide consists of a sequence having at least 90%, at least 95%, at least 96%, at least 97%, at least 98%, or at least 99% sequence identity to a sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16. In some embodiments, the HIV peptide consists of a sequence having SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO: 16. In some embodiments, the HIV peptide is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16. In some embodiments, the HIV peptide is bound to the N-terminus of the at least one MVP protein. In some embodiments, the HIV peptide is genetically linked to the at least one MVP protein or to a mINT domain. In some embodiments, the HIV peptide is genetically linked to the N-terminus of the at least one MVP protein. In some embodiments, the HIV peptide is genetically linked to the at least one MVP protein via a flexible linker. In some embodiments, the HIV peptide is packaged within the internal cavity of the vault particle by, for example, the method according to WO 2016/049122, which is herein incorporated by reference in its entirety.

In some embodiments, the present invention provides a composition comprising at least one HIV peptide vault as described herein. In some embodiments, the composition comprises two or more different types of HIV peptide vaults. In some embodiments, the composition comprises the at least one HIV peptide vault in an immunogenic amount. In some embodiments, the composition comprises the at least one HIV peptide vault in a therapeutically effective amount. In some embodiments, the composition further comprises a pharmaceutically acceptable carrier. In some embodiments, the composition further comprises an adjuvant. In some embodiments, the composition is a pharmaceutical composition. In some embodiments, the composition is a vaccine.

In some embodiments, the present invention provides a method of inducing an immune response in a subject, which comprises administering to the subject an immunogenic amount of one or more HIV peptide vaults as described herein, or a composition according to the present invention. In some embodiments, the present invention provides a method for treating or inhibiting an HIV infection in a subject, which comprises administering to the subject a therapeutically effective amount or an immunogenic amount of one or more HIV peptide vaults as described herein, or a composition according to the present invention. In some embodiments, the therapeutically effective amount or the immunogenic amount is administered as single dose. In some embodiments, the therapeutically effective amount or the immunogenic amount is administered as a series of several doses, e.g., two or more vaccinations separated by a given span of time. In some embodiments, the therapeutically effective amount or the immunogenic amount is administered as three vaccinations, each two weeks apart. In some embodiments, the route of administration is by subcutaneous injection. In some embodiments, the route of administration is by intranasal instillation. In some embodiments, a subject is treated before becoming infected by or exposed to an HIV virus. In some embodiments, the subject to be treated is at risk of being infected by an HIV virus. A subject at risk of being infected by an HIV infection is one who may be or has been exposed to an HIV virus. In some embodiments, the subject to be treated has been infected with an HIV virus. In some embodiments, the HIV virus is HIV-1. In some embodiments, the subject is a non-human primate. In some embodiments, the subject is a human. In some embodiments, the subject is administered one or more antiretroviral therapeutic such as Abacavir (ZIAGEN), Atazanavir (REYATAZ), ATRIPLA (efavirenz, FTC, tenofovir), Darunavir (PREZISTA), DESCOVY (tenofovir alafenamide, emtricitabine), Dolutegravir (TIVICAY), Efavirenz (SUSTIVA), Elvitegravir (VITEKTA), Emtricitabine (FTC, EMTRIVA), Etravirine (INTELENCE), EVIPLERA (rilpivirine, emtricitabine, and tenofovir), EVOTAZ (atazanavir and cobicistat), Fosamprenavir (TELZIR), GENVOYA (elvitegravir, cobicistat, emtricitabine, tenofovir alafenamide (TAF)), KIVEXA (abacavir/3TC), KIVEXA (lamivudine, abacavir), Lamivudine (3TC, EPIVIR), KALETRA (lopinavir, ritonavir), Maraviroc (CELSENTRI), Nevirapine (VIRAMUNE), Odefsey (rilpivirine, emtricitabine, tenofovir alafenamide (TAF)), Raltegravir (ISENTRESS), Rezolsta (darunavir, cobicistat), Rilpivirine (EDURANT), Ritonavir (NORVIR), STRIBILD (elvitegravir, emtricitabine, tenofovir disoproxil, cobicistat), Tenofovir (VIREAD), Triumeq (dolutegravir, abacavir, lamivudine), Truvada (tenofovir, FTC), Zidovudine (AZT, RETROVIR), and the like.

DESCRIPTION OF THE DRAWINGS

This invention is further understood by reference to the drawings wherein:

FIG. 3 shows four conserved regions and three exemplary mosaic representations of each conserved region. For each conserved region, the three exemplary mosaic versions (generated using all curated HIV-1 M-group sequences and the Mosaic Vaccine Tool at the Los Alamos National Laboratory HIV Database) are aligned against reference Glade B consensus sequences. Numbering is per the HXB2 location. As shown, the sequences from top to bottom are: SEQ ID NO: 1 (reference subtype B consensus HIV-1 sequence for a conserved Gag region (cGag1)), SEQ ID NO: 2, SEQ ID NO: 3, SEQ ID NO: 4, SEQ ID NO: 5 (reference subtype B consensus HIV-1 sequence for a second conserved Gag region (cGag2)), SEQ ID NO: 6, SEQ ID NO: 7, SEQ ID NO: 8, SEQ ID NO: 9 (reference subtype B consensus HIV-1 sequence for an Env conserved region (cEnv)), SEQ ID NO: 10, SEQ ID NO: 11, SEQ ID NO: 12, SEQ ID NO: 13 (reference subtype B consensus HIV-1 sequence for a Nef conserved region (cNef)), SEQ ID NO: 14, SEQ ID NO: 15, and SEQ ID NO: 16. Mosaic methods in the art could be used to make one or more mosaic sequences for these conserved regions or others.

FIG. 6 is an example of intracellular cytokine staining flow cytometry after stimulation of mesenteric $CD8^+$ T cells with overlapping 15-mer peptides spanning the stretch in Gag. FIG. 7 is a graph showing the percentages of $CD4^+$ and $CD8^+$ T cells producing interferon-γ in response to these HIV-1 peptides plotted as means and standard deviations (three mice per group). FIG. 8 is a graph showing the percentages of $CD4^+$ and $CD8^+$ T cells producing interferon-γ and interleukin-2 in response to these HIV-1 peptides plotted as means and standard deviations (three mice per group).

DETAILED DESCRIPTION OF THE INVENTION

Figure 1:
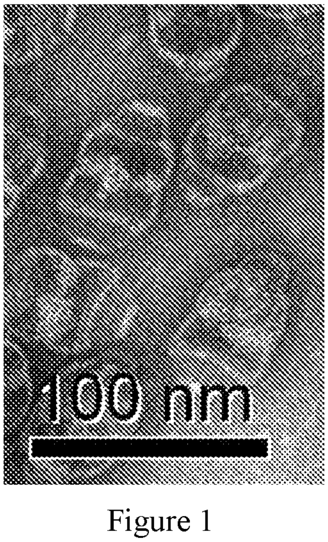
FIG. 1 is a micrograph of vault particles composed of human MVP proteins having an HIV-1 antigenic peptide genetically linked to the N-terminus of the MVP proteins.

The present invention is directed to pharmaceutical compositions, including vaccines, for preventing, treating, inhibiting, or reducing by a Human Immunodeficiency Virus types 1 or 2 (HIV-1 or HIV-2, respectively). In some embodiments, the pharmaceutical composition according to the present invention is a vaccine directed against HIV-1. In some embodiments, the pharmaceutical composition according to the present invention is a vaccine directed against HIV-2. As disclosed herein, compositions according to the present invention comprise a vault particle having at least one HIV peptide bound or genetically linked to at least one MVP protein of the vault particle or packaged within its internal cavity. As used herein, an "HIV peptide vault" refers to a vault particle having at least one HIV peptide bound or genetically linked to at least one MVP protein of the vault particle or packaged within its internal cavity. In some embodiments, the at least one HIV peptide is bound or genetically linked to the N-terminus of the at least one MVP protein. In some embodiments, the at least one HIV peptide is packaged within the internal cavity of the vault particle cell-free methods known in the art. In some embodiments, the at least one HIV peptide is indirectly bound to the at least one MVP protein by being genetically linked to a mINT domain that interacts with the at least one MVP protein. In some embodiments, the at least one HIV peptide is genetically linked, either directly or through a linker, to the at least one MVP protein, preferably at its N-terminus. In some embodiments, the linker is a flexible linker known in the art. In some embodiments, the HIV peptide is an HIV-1 peptide or an HIV-2 peptide, preferably the HIV peptide is an HIV-1 peptide.

As used herein, an "HIV peptide" includes HIV-1 peptides and HIV-2 peptides and refers a protein encoded by an HIV nucleotide sequence and includes peptides from any proteomic region of HIV such as conserved regions, in versions such as consensus, ancestral, or mosaic sequences. Mosaic sequences may be obtained using methods known in the art. See, e.g., Fischer, et al. (2007) Nat Med 13(1):100-106, which is herein incorporated by reference in its entirety. In some embodiments, the HIV nucleotide sequence is obtained or derived from nucleic acids of HIV-1. In some embodiments, the HIV nucleotide sequence is obtained or derived from nucleic acids of HIV-2. In some embodiments, the HIV nucleotide sequence is obtained or derived from an HIV type 1 virus. In some embodiments, the HIV nucleotide sequence is obtained or derived from an HIV type 2 virus. HIV peptides encoded by HIV nucleotide sequences obtained or derived from nucleic acids of HIV-1 and/or HIV-1 viruses are "HIV-1 peptides". HIV peptides encoded by HIV nucleotide sequences obtained or derived from nucleic acids of HIV-2 and/or HIV-2 viruses are "HIV-2 peptides". In some embodiments, the HIV peptide is a fragment of a Gag protein (e.g., Gag-1 or Gag-2), an Env (gp160) protein, or a Nef protein of HIV. In some embodiments, the HIV peptide is a consensus sequence, an ancestral sequence, or a mosaic sequence of the fragment. In some embodiments, the HIV peptide comprises or consists of a sequence selected from the group consisting of:

(SEQ ID NO: 1)
SPRTLNAWVKVVEEKAFSPEVIPMFSALSEGATPQDLNTMLNTVGGHQAA
MQMLKETINEEAAEWDR;

(SEQ ID NO: 2)
TPRTLNAWVKVVEEKAFSPEVIPMFTALSEGATPSDLNTMLNTIGGHQAA
MQMLKDTINEEAAEWDR;

(SEQ ID NO: 3)
SARTLNAWVKVVEEKGFNPEVIPMFSALSEGATPQDLNTMLNTVGGHQAA
MQMLKETINEEAAEWDR;

(SEQ ID NO: 4)
SPRILNAWVKVIEEKAFSPEVIPMFSALAEGATPQDLNMMLNIVGGHQAA
MQMLKDTINDEAAEWDR;

(SEQ ID NO: 5)
NPPIPVGEIYKRWIILGLNKIVRMYSPISILDIRQGPKEPFRDYVDRFYK
TLRAEQASQEVKNWMTETLLVQNANPDCKTILKALG;

(SEQ ID NO: 6)
NPPIPVGDIYKRWIILGLDKIVRMYSPISILDIRQGPKEPFRDYVDRFFK
VLRAEQATQDVKNWMTDILLVQNANPDCKTILRALG;

(SEQ ID NO: 7)
NPPVPVGEIYKRWIVLGLNKIVRMYSPVSILDIRQGPKESFRDYVDRFYK
TLRAEQASQDVKNWMTETLLVQNSNPDCKTILKALG;

(SEQ ID NO: 8)
NPPIPVGEIYKRWIILGLNKIVRMYSPVSILDIKQGPKEPFRDYVDRFFK
ILRAEQATQEVKNWMTETLLVQNANPDCKSILKALG;

(SEQ ID NO: 9)
GFLGAAGSTMGAASMILTVQARQLLSGIVQQQNNLLRAIEAQQHLLQLTV
WGIKQLQARVLAVERYLKDQQLLGIWGCSGKLICTT;

(SEQ ID NO: 10)
GFLGVAGSTMGAASITLIVQARQLLSGIVQQQSNLLRAIEAQQHLLKLIV
WGIKQLQTRVLAIERYLKDQQLLGLWGCSGKLICPT;

(SEQ ID NO: 11)
GFLGTAGSTMGAASLTLIVQARQVLSGIVQQQNNLLRAIEAQQHMLQLTV
WGIKQLQARVLAVERYLKDQQLLGIWGCSGKIICTT;

(SEQ ID NO: 12)
GFLGAAGSTMGAASMILTVQARLLLSGIVQQQSNLLKAIEAQQHLLQLTV
WGIKQLQARILAVERYLRDQQLLGIWGCSGKLICTT;

(SEQ ID NO: 13)
RQDILDLWVYHTQGYFPDWQNYTPGPGIRYPLIFGWCFKLVPV;

(SEQ ID NO: 14)
RQEILDLWVYHTQGFFPDWQNYTPGPGIRYPLIFGWCYKLVPV;

(SEQ ID NO: 15)
RKDILDLWVYNTQGYFPDWHNYTPGPGIRFPLIFGWCFKLVPV;
and (SEQ ID NO: 16)
RQDILDLWVYHTQGYFPDWQNYTPGPGVRYPLIFGWCFELVPV.

In some embodiments, the HIV peptide comprises or consists of a sequence having at least 90%, at least 95%, at least 96%, at least 97%, at least 98%, or at least 99% sequence identity to a sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16. In some embodiments, the HIV peptide comprises or consist of a sequence having at least 90%, at least 95%, at least 96%, at least 97%, at least 98%, or at least 99% sequence identity to a sequence selected from the group consisting of: SEQ ID NO: 2, SEQ ID NO: 3, SEQ ID NO: 4, SEQ ID NO: 6, SEQ ID NO: 7, SEQ ID NO: 8, SEQ ID NO: 10, SEQ ID NO: 11, SEQ ID NO: 12, SEQ ID NO: 14, SEQ ID NO: 15, and SEQ ID NO: 16. In some embodiments, the HIV peptide comprises or consists of a sequence having at least 90%, at least 95%, at least 96%, at least 97%, at least 98%, or at least 99% sequence identity to a sequence selected from the group consisting of: SEQ ID NO: 1, SEQ ID NO: 5, SEQ ID NO: 9, and SEQ ID NO: 13.

As used herein, the term percent sequence "identity" refers to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (ncbi.nlm.nih.gov).

As used herein, an "HIV epitope" refers to an antigenic determinant of a human immunodeficiency virus and includes those known in the art.

Figure 2:
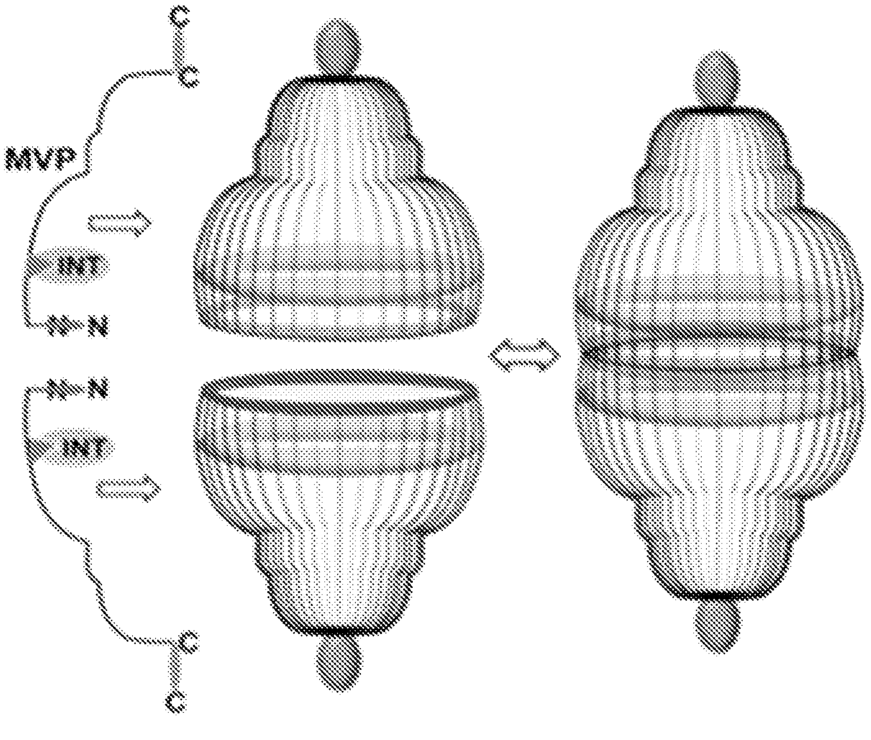
FIG. 2 schematically shows the structure of a vault shell, comprised of the major vault protein (MVP) in 78 repeating units, with N-termini facing inside the vault particle at the waist, and C-termini at the outer poles. The line through the first N drawn to the second N indicates a genetically linked extension of the N-terminus with an antigenic peptide.

FIG. 1 shows a micrograph of representative HIV peptide vaults according to the present invention and FIG. 2 schematically shows the structure of an HIV peptide vault. As used herein, a "vault particle" refers to a complex of MVP proteins arranged to form a structure having ovoid shape and an internal cavity. The vault particles additionally comprise one or more VPARP proteins, one or more TEP1 proteins, and/or RNA. As used herein, an "MVP protein" refers to a protein that has 90-100%, preferably 95-100%, sequence identity to a major vault protein and is capable of forming a part of a vault. Examples of major vault proteins are provided in the NCBI protein database (available on the Internet, ncbi.nlm.nih.gov/protein) and include GI: 41055865 (rat), GI: 239052674 (mouse), and GI: 15990478 (human). MVP proteins can be synthetic, mutated, modified, human, animal (e.g., rat MVP), etc. In some embodiments, the one or more MVP proteins of the vault particles according to the present invention have 90-100%, 95-100%, 97-99%, or 100% sequence identity to GI: 15990478 (human). As used herein, a "VPARP protein" refers to a protein that has 90-100%, preferably 95-100%, sequence identity to a vault poly ADP-ribose polymerase and is capable of forming a part of a vault. Examples of VPARP proteins are provided in the NCBI protein database (available on the Internet, ncbi.nlm.nih.gov/protein) and include GI: 149064059 (rat), GI: 281485553 (mouse), and GI: 112789550 (human). VPARP proteins can be synthetic, mutated, modified, human, animal (e.g., rat VPARP), etc. In some embodiments, the one or more VPARP proteins of the vault particles according to the present invention have 90-100%, 95-100%, 97-99%, or 100% sequence identity to GI: 112789550 (human). As used herein, a "TEP1 protein" refers to a protein that has 90-100%, preferably 95-100%, sequence identity to a telomerase/vault associated protein 1 and is capable of forming a part of a vault. Examples of TEP1 proteins are provided in the NCBI protein database (available on the Internet, ncbi.nlm.nih.gov/protein) and include GI: 12018250 (rat), GI: 6678285 (mouse), and GI: 21536371 (human). TEP1 proteins can be synthetic, mutated, modified, human, animal (e.g., rat TEP1), etc. In some embodiments, the one or more TEP1 proteins of the vault particles according to the present invention have 90-100%, 95-100%, 97-99%, or 100% sequence identity to GI: 21536371 (human). As used herein, a "mINT domain" refers to the major vault protein interaction domain (mINT) of a VPARP protein or portion thereof that is capable of interacting with MVP proteins of naturally occurring vaults. The vault particles may be made using cell-based methods or cell-free methods known in the art. In some embodiments, the vault particles are made using cell-free methods, see, for example, WO 2016/049122, which is herein incorporated by reference in its entirety.

As disclosed herein, HIV peptide vaults are highly immunogenic and result in systemic and mucosal immunity in subjects when administered thereto. Therefore, the present invention provides immunogenic compositions and vaccine compositions which comprise a vault particle having at least one HIV peptide bound to at least one MVP protein of the vault particle.

Compositions of the present invention, including pharmaceutical compositions and vaccines, may include one type of HIV peptide vault or two or more different types of HIV peptide vaults, e.g., HIV peptide vaults having different HIV peptides, or HIV peptide vaults having the same HIV peptide but some having the HIV peptide genetically linked to the MVP proteins and some having the HIV peptide genetically linked to mINT domains, etc.

The term "pharmaceutical composition" refers to a composition suitable for pharmaceutical use in a subject. A pharmaceutical composition generally comprises an effective amount of an active agent, e.g., an HIV peptide vault according to the present invention, and a pharmaceutically acceptable carrier, e.g., a buffer, adjuvant, and the like. The term "effective amount" refers to a dosage or amount sufficient to produce a desired result. The desired result may comprise an objective or subjective improvement in the recipient of the dosage or amount, e.g., long-term survival, decrease in viremia, effective prevention of a disease state, and the like.

One or more HIV peptide vaults according to the present invention may be administered, preferably in the form of pharmaceutical compositions, to a subject. Preferably the subject is mammalian, more preferably, the subject is human. Preferred pharmaceutical compositions are those comprising at least one HIV peptide vault in an immunogenic amount or a therapeutically effective amount, and a pharmaceutically acceptable vehicle.

Vaccines according to the present invention provide a protective immune response when administered to a subject. As used herein, a "vaccine" according to the present invention is a pharmaceutical composition that comprises an immunogenic amount of at least one HIV peptide vault and provides a protective immune response when administered to a subject. The protective immune response may be complete or partial, e.g., a reduction in symptoms as compared with an unvaccinated subject.

As used herein, an "immunogenic amount" is an amount that is sufficient to elicit an immune response in a subject and depends on a variety of factors such as the immunogenicity of the given HIV peptide vault, the manner of administration, the general state of health of the subject, and the like. The typical immunogenic amounts for initial and boosting immunizations for therapeutic or prophylactic administration may range from about 120 μg to 8 mg per kilogram of body weight of a subject. For example, the typical immunogenic amount for initial and boosting immunization for therapeutic or prophylactic administration for a human subject of 70 kg body weight ranges from about 8.4 mg to about 560 mg, preferably about 10-100 mg, more preferably about 10-20 mg, per about 65-70 kg body weight of a subject. Examples of suitable immunization protocols include an initial immunization injection (time 0), followed by booster injections at 4, and/or 8 weeks, which these initial immunization injections may be followed by further booster injections at 1 or 2 years if needed.

As used herein, a "therapeutically effective amount" refers to an amount that may be used to treat, prevent, or inhibit a given condition, such as an HIV infection, in a subject as compared to a control. Again, the skilled artisan will appreciate that certain factors may influence the dosage required to effectively treat a subject, including the degree of exposure to HIV, previous treatments, the general health and age of the subject, and the like. A therapeutically effective amount may be readily determined by conventional methods known in the art. It should be noted that treatment of a subject with a therapeutically effective amount or an immunogenic amount, may be administered as a single dose or as a series of several doses.

The compositions of the present invention may include an adjuvant. As used herein, an "adjuvant" refers to any substance which, when administered with or before a pharmaceutically active agent, such as a HIV peptide vault according to the present invention, aids the pharmaceutically active agent in its mechanism of action. Thus, an adjuvant in a vaccine according to the present invention is a substance that aids the at least one HIV peptide vault in eliciting an immune response. Suitable adjuvants include incomplete Freund's adjuvant, alum, aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, nor-MDP), N-acetylmuramyl-Lalanyl-D-isoglutaminyl-L-alanine-2-(1'-2'-dipa-lmitoyl-sn-glycero-3-hydroxyphosphoryloxy)-ethylamine (CGP 19835A, MTP-PE), and RIBI, which comprise three components extracted from bacteria, monophosphoryl lipid A, trehalose dimycolate and cell wall skeleton (NPL+TDM+CWS) in a 2% squalene/Tween 80 emulsion. The effectiveness of an adjuvant may be determined by methods in the art.

Pharmaceutical compositions of the present invention may be formulated for the intended route of delivery, including intravenous, intramuscular, intra peritoneal, subcutaneous, intraocular, intrathecal, intraarticular, intrasynovial, cisternal, intrahepatic, intralesional injection, intracranial injection, infusion, and/or inhaled routes of administration using methods known in the art. Pharmaceutical compositions according to the present invention may include one or more of the following: pH buffered solutions, adjuvants (e.g., preservatives, wetting agents, emulsifying agents, and dispersing agents), liposomal formulations, nanoparticles, dispersions, suspensions or emulsions as well as sterile powders for reconstitution into sterile injectable solutions or dispersions. The compositions and formulations of the present invention may be optimized for increased stability and efficacy using methods in the art. See, e.g., Carra et al. (2007) Vaccine 25:4149-4158, which is herein incorporated by reference.

The compositions of the present invention may be administered to a subject by any suitable route including oral, transdermal, subcutaneous, intranasal, inhalation, intramuscular, and intravascular administration. It will be appreciated that the preferred route of administration and pharmaceutical formulation will vary with the condition and age of the subject, the nature of the condition to be treated, the therapeutic effect desired, and the particular polypeptide, polynucleotide, or antibody used.

As used herein, a "pharmaceutically acceptable vehicle" or "pharmaceutically acceptable carrier" are used interchangeably and refer to and include any and all solvents, dispersion media, coatings, antibacterial and antifungal agents, isotonic and absorption delaying agents, and the like, that are compatible with pharmaceutical administration and comply with the applicable standards and regulations, e.g., the pharmacopeial standards set forth in the United States Pharmacopeia and the National Formulary (USP-NF) book, for pharmaceutical administration. Thus, for example, unsterile water is excluded as a pharmaceutically acceptable carrier for, at least, intravenous administration. Pharmaceutically acceptable vehicles include those known in the art. See, e.g., Remington: The Science and Practice of Pharmacy. $20^{th}$ ed. (2000) Lippincott Williams & Wilkins. Baltimore, Md., which is herein incorporated by reference.

The pharmaceutical compositions of the present invention may be provided in dosage unit forms. "Dosage unit form" as used herein refers to physically discrete units suited as unitary dosages for the subject to be treated; each unit containing a predetermined quantity of active compound calculated to produce the desired therapeutic effect in association with the required pharmaceutically acceptable carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of the HIV peptide vaults according to the instant invention and compositions thereof can be determined by standard pharmaceutical procedures in cell cultures or experimental animals. For example, one may determine the lethal dose, $LC_{50}$ (the dose expressed as concentration×exposure time that is lethal to 50% of the population) or the $LD_{50}$ (the dose lethal to 50% of the population), and the $ED_{50}$ (the dose therapeutically effective in 50% of the population) by conventional methods in the art. The dose ratio between toxic and therapeutic effects is the therapeutic index and it can be expressed as the ratio $LD_{50}/ED_{50}$. HIV peptide vaults which exhibit large therapeutic indices are preferred. While HIV peptide vaults that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, a therapeutically effective amount and/or dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography. Additionally, a suitable dosage for a given subject can be determined by an attending physician or other qualified medical personnel, based on various clinical factors.

In some embodiments, the present invention is directed to kits which comprise one or more HIV peptide vaults, optionally in a composition or in combination with one or more additional therapeutic agents such as an antiretroviral therapeutic, packaged together with one or more reagents or drug delivery devices for preventing, inhibiting, reducing, or treating an HIV infection in a subject. Such kits include a carrier, package, or container that may be compartmentalized to receive one or more containers, such as vials, tubes, and the like. In some embodiments, the kits optionally include an identifying description or label or instructions relating to its use. In some embodiments, the kits comprise the one or more HIV peptide vaults, optionally in one or more unit dosage forms, packaged together as a pack and/or in drug delivery device, e.g., a pre-filled syringe. In some embodiments, the kits include information prescribed by a governmental agency that regulates the manufacture, use, or sale of compounds and compositions according to the present invention.

The following examples are intended to illustrate but not to limit the invention.

EXAMPLES

Although SEQ ID NO:2 was used as the exemplary HIV peptide for the immunogenic data provided herein, any peptide that results in an antibody response against HIV by itself or with a vault particle as an HIV peptide vault may be used in accordance with the invention.

Selection of Peptides of the HIV-1 Proteome

Four candidate proteome regions of HIV-1 were obtained by scanning for amino acid variability (Shannon Entropy) across all available M-group HIV-1 sequences in the Los Alamos National Laboratory HIV Sequence Database. See Yang (2009) PLoS ONE 4(1):e7338, which is herein incorporated by reference. These regions included Gag 148-214 (cGag-1), Gag 250-335 (cGag-2), Env 521-606 (cEnv), and Nef 106-148 (cNef). Because these candidate peptides were not perfectly conserved across all HIV isolates, a computing tool from the Los Alamos National Laboratory (Thurmond et al, 2008, Bioinformatics 24 (14): 1639-1640) was used to create sets of three HIV mosaic sequences for each of the above regions to maximize representation of all 9-mer sequences within a broad set of HIV-1 sequences spanning virus variability across the world. These sets of three mosaics per region (e.g., for cGag-1: versions cGag-1M1, cGag-1M2, cGag-1M3 are shown in FIG. 3. These computed sets of mosaic sequences provide coverage of over 90% of all possible stretches of 9-mer sequences within the HIV-1 sequences representing virus variability across the world. Subsequently, these HIV peptide sequences were shown to be highly immunogenic in rhesus macaques in a vaccination study using DNA and viral vectors. See Yang, et al. (2015) J Virol 89(2):1195-1204, which is herein incorporated by reference in its entirety.

Figure 4:
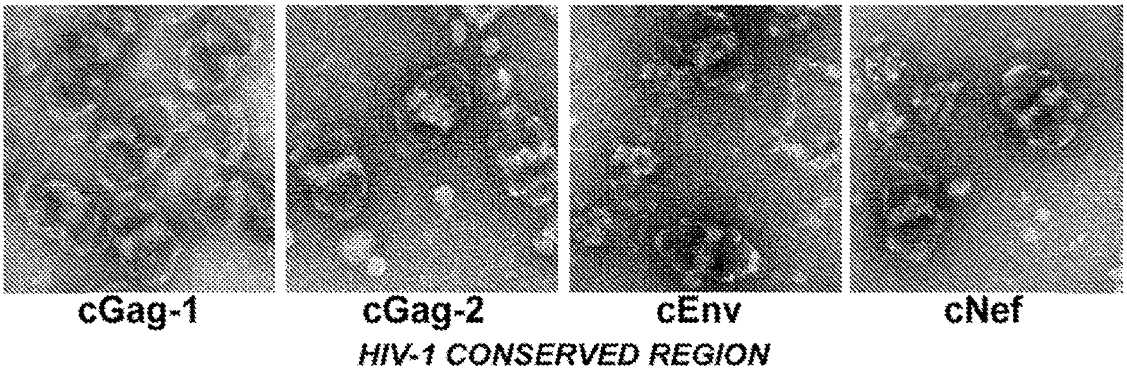
FIG. 4 shows electron micrographs of vaults containing conserved regions of HIV-1. The indicated HIV peptides were genetically linked to the N-terminus of human major vault protein (MVP) via a linker sequence (GGGGSGGGGSGGGGS, SEQ ID NO: 17). These nucleotide sequences encoding the HIV-MVP fusion proteins were delivered via baculovirus vector to Sf9 insect cells for expression and the engineered vault particles were purified from cell lysates using sucrose gradient purification methods known in the art. From left to right, these vaults contain SEQ ID NO: 1, SEQ ID NO: 4, SEQ ID NO: 7, SEQ ID NO: 10 bound to the N-termini of their MVP proteins.

Generation of Human Vaults that Deliver Conserved Regions of the HIV-1 Proteome HIV peptide vaults consisting of human MVP proteins having the HIV peptides FIG. 3 recombinantly linked to the N-terminus via a flexible linker (GGGGSGGGGSGGGGS, SEQ ID NO: 17) of the MVP proteins were engineered using methods in the art. The linker sequence enhanced the yield of the HIV peptide vaults, presumably by reducing steric hindrance from the added sequences. Genetic constructs encoding the HIV-MVP fusion proteins were delivered to insect Sf9 cells using a standard baculovirus vector and methods in the art for cell-based vault expression and purification were used. FIG. 4 shows electron micrographs of the HIV peptide vaults.

Figure 5:
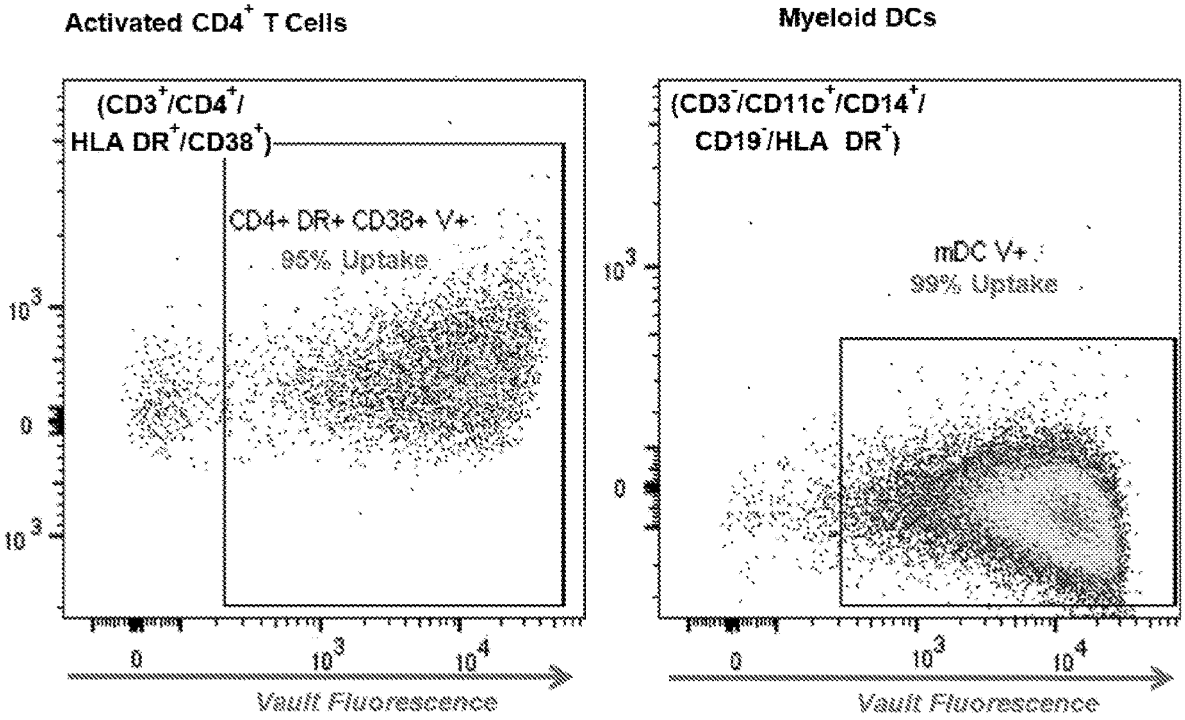
FIG. 5 are graphs showing the uptake of fluorescent labeled recombinant human unmodified vaults by antigen-presenting cells. These were added to human peripheral blood mononuclear cells (PBMCs) for 2 hours, followed by flow cytometry. Microscopy showed endosomal uptake and rapid escape into cytoplasm (not shown).

Uptake by Human Antigen Presenting Cells (APCs) Demonstrates Remarkably Efficient Uptake Uptake and processing of proteins by antigen presenting cells (APCs) is crucial for generating new immune responses, particularly T cell responses. Using methods in the art, the HIV peptide vaults were taken up by human peripheral blood mononuclear cells. The uptake of the HIV peptide vaults was assessed using fluorescent labels and flow cytometry. As shown in FIG. 5, the uptake was remarkably efficient in activated $CD4^+$ T cells and myeloid dendritic cells, approaching 100% in a 2 hour incubation.

Vaccination Studies

Figure 6:
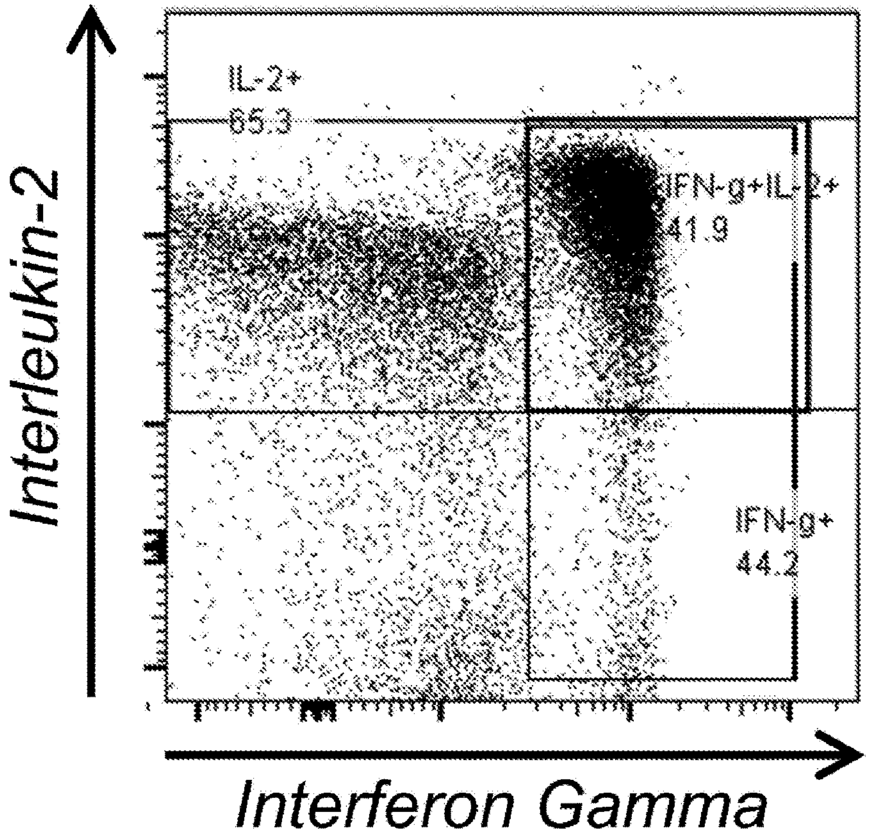
FIG. 6 to FIG. 8 are graphs evidencing that vault particles having HIV-1 peptides bound thereto yield systemic and mucosal polyfunctional T cell responses. Mice (C57BL6) were given subcutaneous injections (SC) or intranasal instillations (IN) of human recombinant vaults (100 μg) with or without the cGag-1 sequence (SEQ ID NO: 2) at weeks 0, 2, and 4, followed by harvesting of splenic and mesenteric T cells at week 6.
Figure 7:
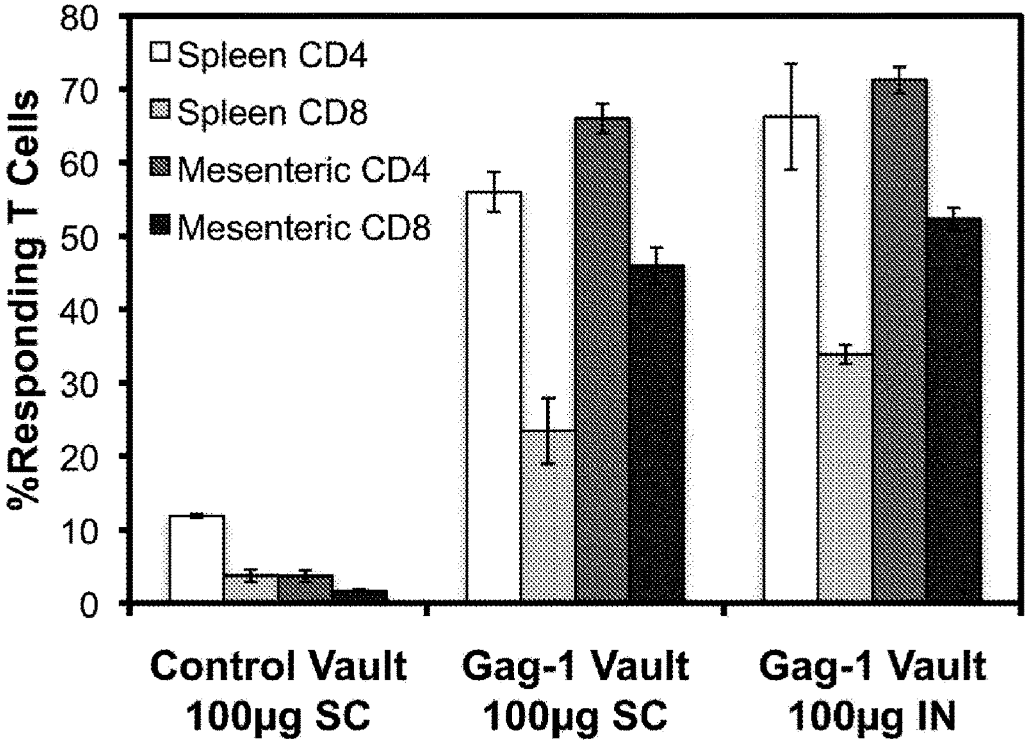
Figure 8:
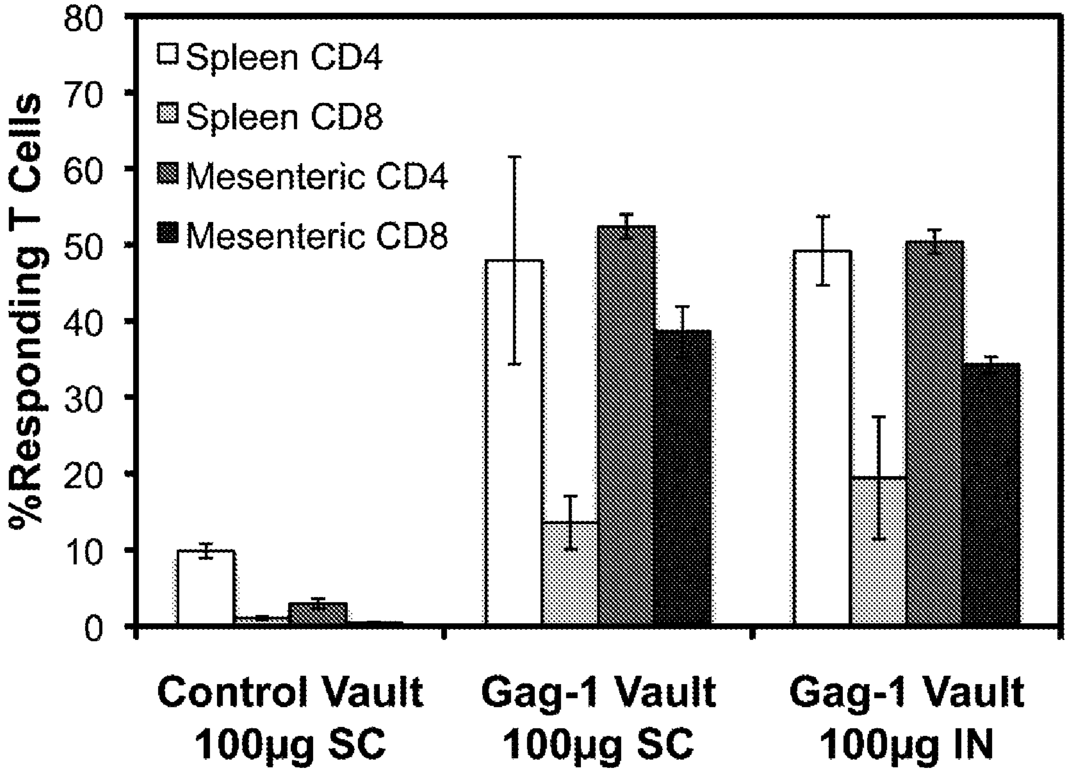

Systemic and mucosal immune responses in mice vaccinated with HIV peptide vaults (with HIV peptides having SEQ ID NO: 2 genetically linked to the MVP proteins of vault particles) were compared to that of mice vaccinated with control vaults (vault particle without any HIV peptide linked thereto). Three vaccinations separated by 2 weeks were given via subcutaneous injection or intranasal inoculation, and cellular immune responses were assessed by intracellular cytokine staining and flow cytometry for responses against the cGag-1 sequence delivered by the HIV peptide vault. The results of FIG. 6, FIG. 7, and FIG. 8 show remarkably high frequency of responding T cells in both systemic (spleen) and mucosal (mesenteric) compartments from both inoculation routes. Note that when measuring cellular immune responses in persons with HIV-1 infection, the magnitudes of responses against HIV-1 peptides are typically <1% and measured as low as 0.005% of all T cells, while the observed frequencies of cells against the peptides are 10-70% of all T cells.

Figure 9:
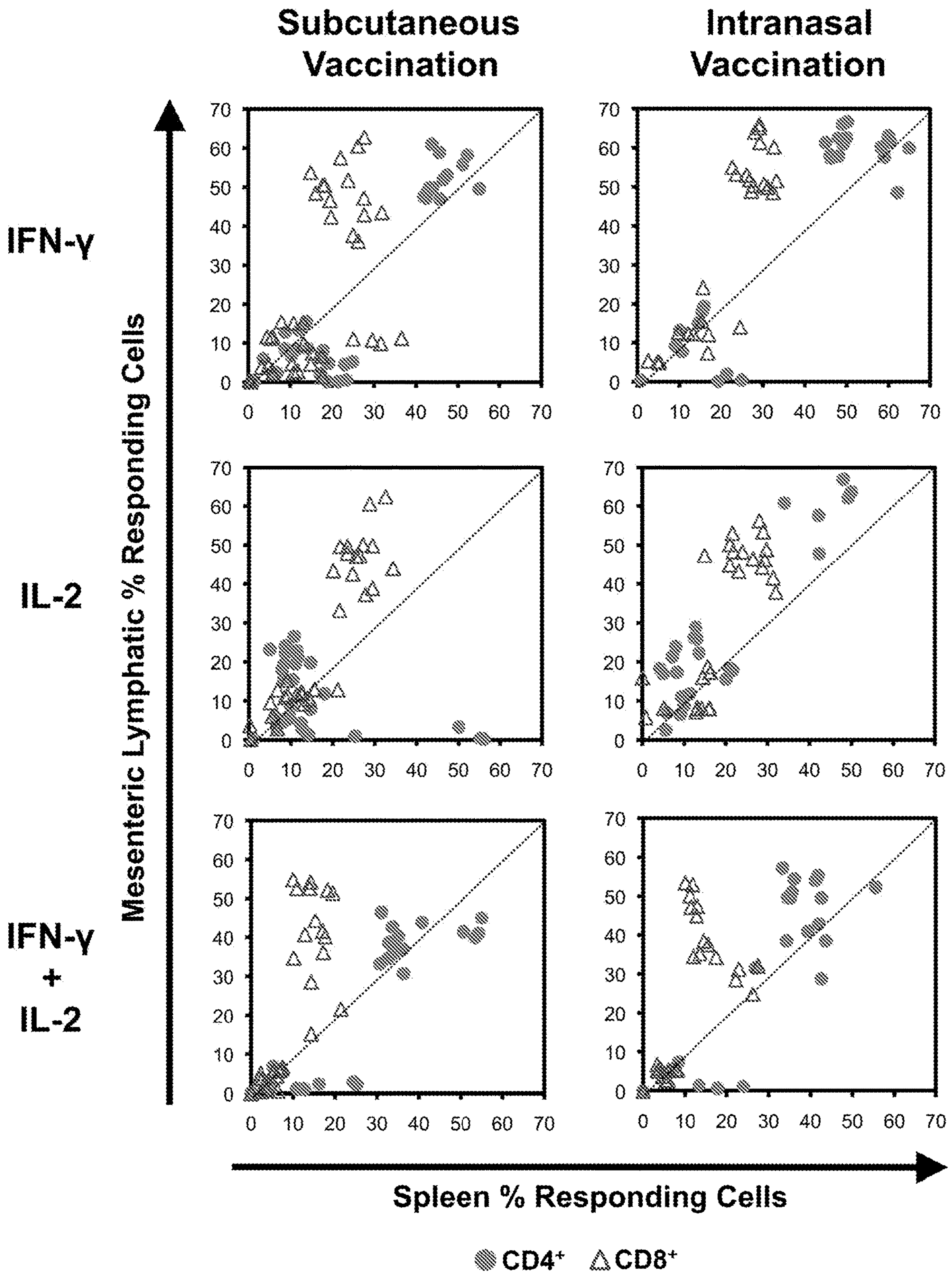
FIG. 9 are plots comparing the results from subcutaneous injection versus intranasal instillation vaccination methods. These plots show data from 4 separate experiments where Gag-1 vaults were given as subcutaneous injection (first column) or intranasal vaccinations (second column) in doses ranging from 1 to 100 μg to C57B6 mice as before (three vaccinations separated by 2 weeks each). Each point is the mean response of 3 mice at two weeks after the third dose. Three readouts are shown in terms of cytokine production in response to Gag-1 peptides (three rows: interferon gamma alone, interleukin 2 alone, or production of both). Solid dots indicate CD4+ T cells and open triangles indicated CD8+ T cells responding to Gag-1. In each plot, the percentage of responding cells is indicated for mesenteric lymph nodes (Y axis) and spleen (X axis).
Figure 10:
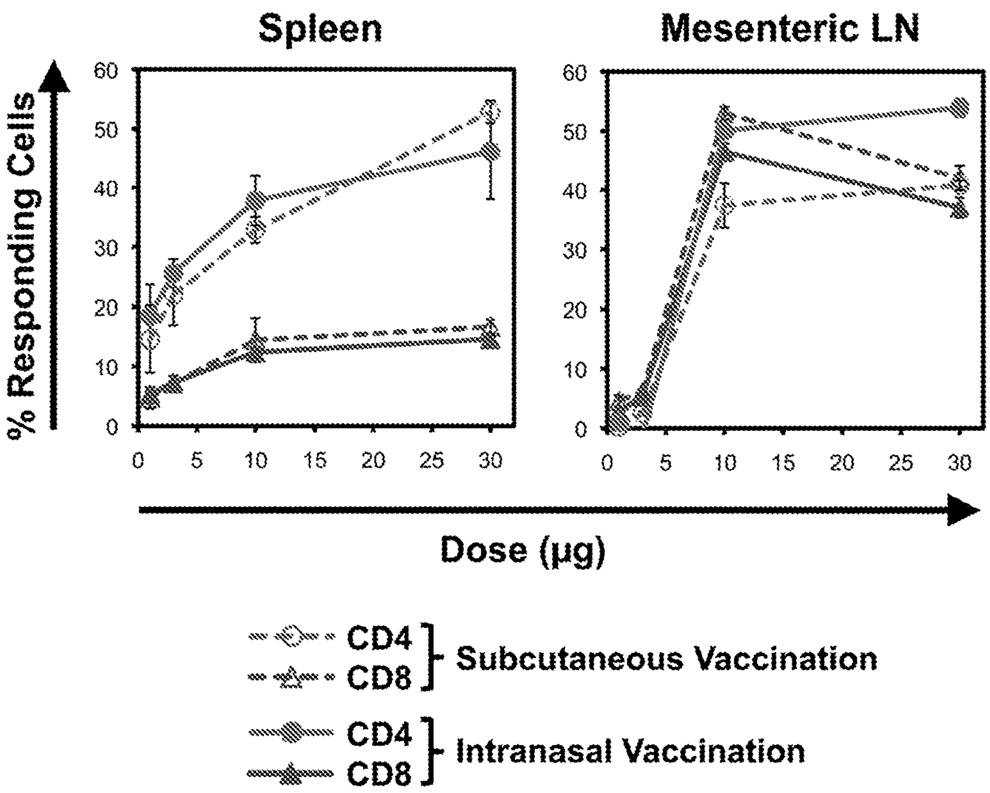
FIG. 10 are graphs showing the percent of cells responding to Gag-1 vaults in response to subcutaneous and intranasal vaccination. These plots show an experiment where mice were vaccinated with different doses of Gag-1 vaults, 3, 10, and 30 μg doses each two weeks apart. The graphs indicate the percentage of cells responding to Gag-1 measured by interferon gamma and IL-2 co-production. Each point is the mean of 3 mice after the third dose; error bars are 1 S.D. The results show that maximal effect is probably achieved between 3 and 10 μg dose per mouse.
Figure 11:
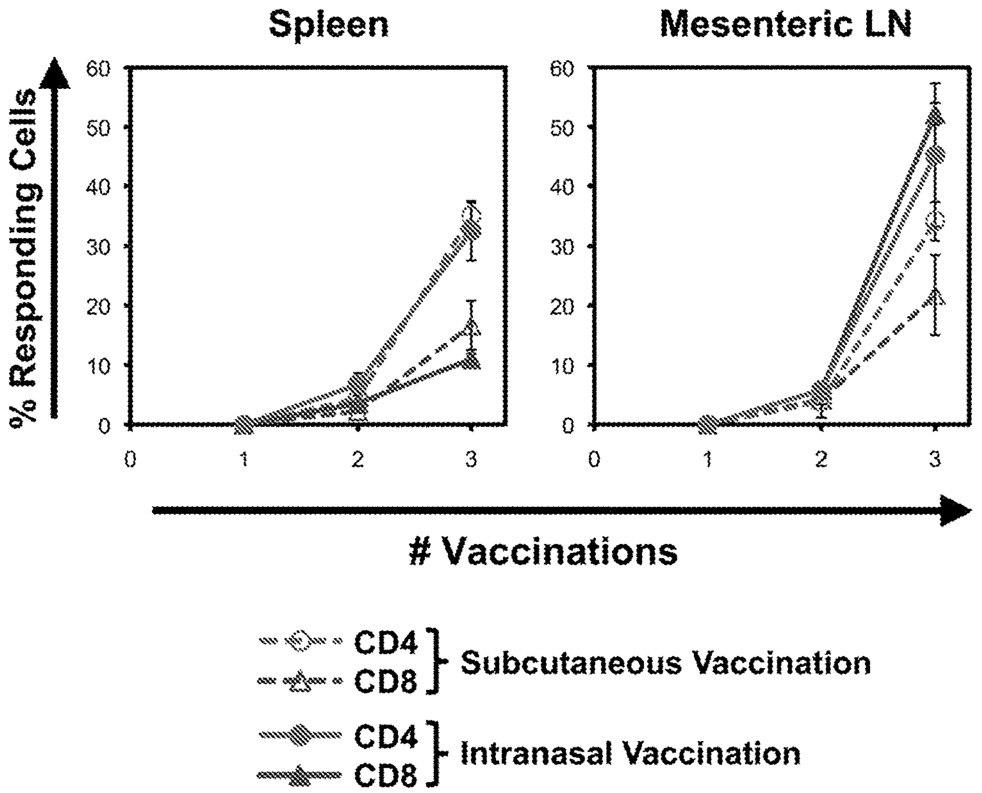
FIG. 11 are graphs showing that the percent of responding cells in response to vaccination dose numbers. These plots show an experiment where mice were vaccinated with different numbers of doses each two weeks apart, from one to three doses. Each point is the mean of three mice at two weeks after the last dose; error bars are 1 S.D.
Figure 12:
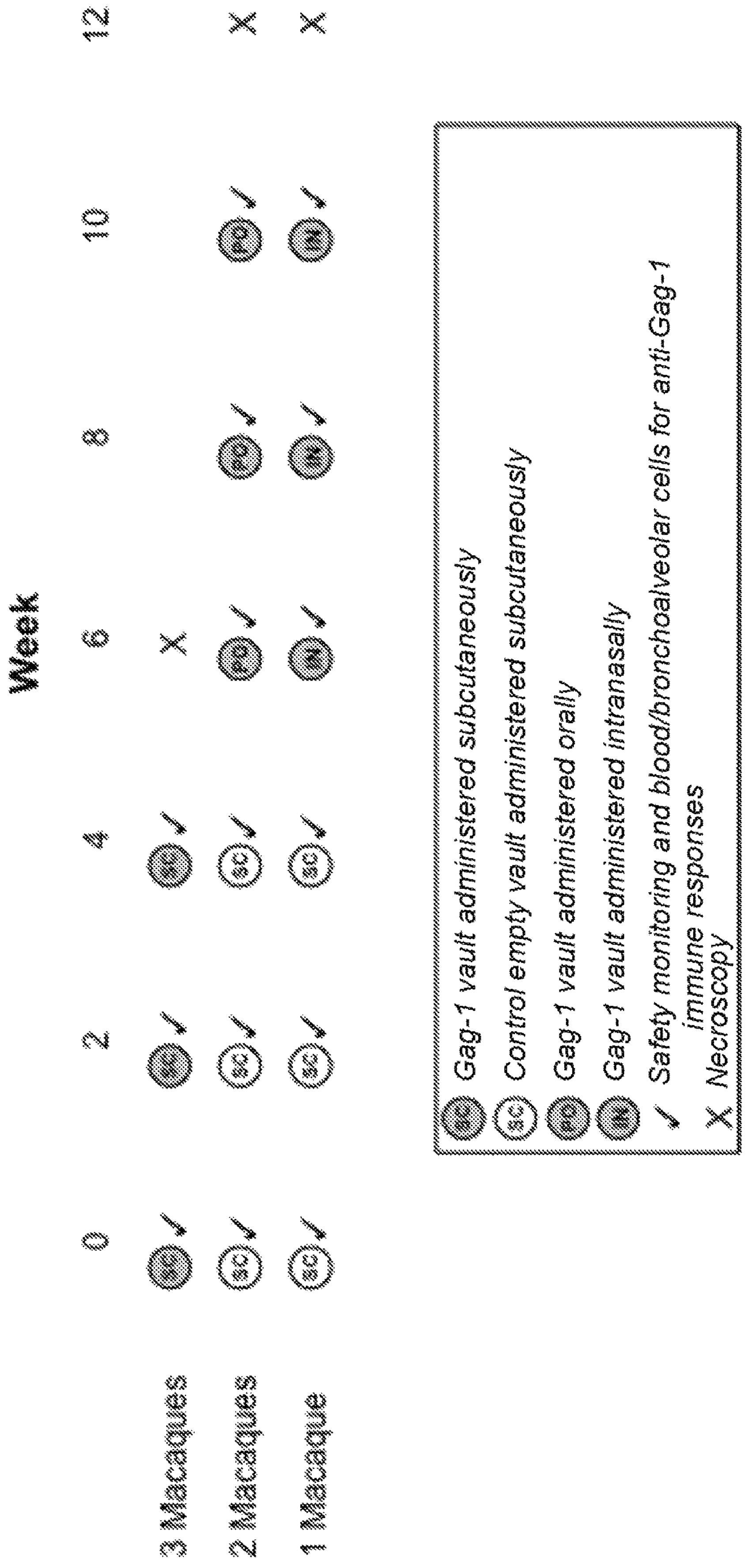
FIG. 12 schematically shows the protocol for a vaccine immunogenicity and safety test of the Gag-1 vault in macaques that is underway. Gag-1 vaults and empty vaults (control) have been purified by HPLC. A test group of three animals will receive the Gag-1 vaults and a control group of three animals will receive control (control vaults). The vaults will be administered subcutaneously to animals in three doses, two weeks apart each, and each dose will be 3 mg (proportional to 10 μg dose in a mouse) of vault. Then the animals belonging to the control group will be vaccinated with the Gag-1 vaults, two orally and one intranasally.

The data summarized in FIG. 9 suggest that (1) overall, the responses in the mesenteric compartment are higher frequency than the splenic compartment for both vaccination routes (compare numbers of dots below versus above the dotted lines); and (2) intranasal vaccination may be more immunogenic for the mesenteric compartment than subcutaneous vaccination for CD4+ T cell responses (compare left panels to right panels). The data in FIG. 10 indicate the percentage of cells responding to Gag-1 measured by interferon gamma production and that the maximal effect is probably achieved between 3 and 10 μg dose per mouse. The data in FIG. 11 indicate that the maximal effect is not attained until at least three doses, although there are definite responses after the second dose that have magnitudes similar to the recombinant Adenovirus serotype 5 vaccine in mice, which the Adenovirus serotype 5 vaccine was advanced to testing in macaques and then humans.

All scientific and technical terms used in this application have meanings commonly used in the art unless otherwise specified.

As used herein, the term "subject" includes humans and non-human animals. The term "non-human animal" includes all vertebrates, e.g., mammals and non-mammals, such as non-human primates, horses, sheep, dogs, cows, pigs, chickens, and other veterinary subjects and test animals.

The use of the singular can include the plural unless specifically stated otherwise. As used in the specification and the appended claims, the singular forms "a", "an", and "the" can include plural referents unless the context clearly dictates otherwise. As used herein, "and/or" means "and" or "or". For example, "A and/or B" means "A, B, or both A and B" and "A, B, C, and/or D" means "A, B, C, D, or a combination thereof" and said "combination thereof" means any subset of A, B, C, and D, for example, a single member subset (e.g., A or B or C or D), a two-member subset (e.g., A and B; A and C; etc.), or a three-member subset (e.g., A, B, and C; or A, B, and D; etc.), or all four members (e.g., A, B, C, and D).

The phrase "comprises or consists of" is used as a tool to avoid excess page and translation fees and means that in some embodiments the given thing at issue comprises something, and in some embodiments the given thing at issue consists of something. For example, the sentence "In some embodiments, the composition comprises or consists of a A" is to be interpreted as if written as the following two separate sentences: "In some embodiments, the composition comprises A. In some embodiments, the composition consists of A." Similarly, sentence reciting a string of alternates is to be interpreted as if a string of sentences were provided such that each given alternate was provided in a sentence by itself. For example, the sentence "In some embodiments, the composition comprises A, B, or C" is to be interpreted as if written as the following three separate sentences: "In some embodiments, the composition comprises A. In some embodiments, the composition comprises B. In some embodiments, the composition comprises C."

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. An HIV peptide vault which comprises a vault particle comprising a complex of MVP proteins and at least one HIV peptide bound or genetically linked to at least one MVP protein or packaged within an internal cavity of the vault particle, wherein the at least one HIV peptide comprises a sequence having at least 96% identity to SEQ ID NO: 2, SEQ ID NO: 3, SEQ ID NO: 4, SEQ ID NO: 6, SEQ ID NO: 7, SEQ ID NO: 8, SEQ ID NO: 10, SEQ ID NO: 11, SEQ ID NO: 12, SEQ ID NO: 14, SEQ ID NO: 15, or SEQ ID NO: 16.

2. An HIV peptide vault which comprises a vault particle comprising a complex of MVP proteins and at least one HIV peptide bound or genetically linked to the N-terminus of at least one MVP protein, wherein the at least one HIV peptide comprises a sequence having at least 96% identity to SEQ ID NO: 2, SEQ ID NO: 3, SEQ ID NO: 4, SEQ ID NO: 6, SEQ ID NO: 7, SEQ ID NO: 8, SEQ ID NO: 10, SEQ ID NO: 11, SEQ ID NO: 12, SEQ ID NO: 14, SEQ ID NO: 15, or SEQ ID NO: 16.

3. The HIV peptide vault according to claim 1, wherein the HIV peptide consists of a sequence having at least at least 96% sequence identity to a sequence selected from the group consisting of: SEQ ID NO: 2, SEQ ID NO: 3, SEQ ID NO: 4, SEQ ID NO: 6, SEQ ID NO: 7, SEQ ID NO: 8, SEQ ID NO: 10, SEQ ID NO: 11, SEQ ID NO: 12, SEQ ID NO: 14, SEQ ID NO: 15, and SEQ ID NO: 16.

4. The HIV peptide vault according to claim 1, wherein the HIV peptide consists of a sequence having SEQ ID NO: 2, SEQ ID NO: 3, SEQ ID NO: 4, SEQ ID NO: 6, SEQ ID NO: 7, SEQ ID NO: 8, SEQ ID NO: 10, SEQ ID NO: 11, SEQ ID NO: 12, SEQ ID NO: 14, SEQ ID NO: 15, and SEQ ID NO: 16.

5. The HIV peptide vault according to claim 1, wherein the HIV peptide is bound to the N-terminus of the at least one MVP protein.

6. The HIV peptide vault according to claim 1, wherein the HIV peptide is genetically linked to the at least one MVP protein or to a mINT domain.

7. The HIV peptide vault according to claim 1, wherein the HIV peptide is genetically linked to the N-terminus of the at least one MVP protein.

8. The HIV peptide vault according to claim 7, wherein the HIV peptide is genetically linked to the at least one MVP protein via a flexible linker.

9. A composition comprising at least one HIV peptide vault according to claim 1.

10. The composition according to claim 9, wherein the at least one HIV peptide vault is present in an immunogenic amount.

11. The composition according to claim 9, and further comprising a pharmaceutically acceptable carrier.

12. A vaccine comprising at least one HIV peptide vault according to claim 1.

13. The vaccine according to claim 12, and further comprising an adjuvant.

14. A method of inducing an immune response in a subject, which comprises administering an immunogenic amount of the HIV peptide vault according to claim 1.

* * * * *

SEQUENCE LISTING

```
<160> NUMBER OF SEQ ID NOS: 17

<210> SEQ ID NO 1
<211> LENGTH: 67
<212> TYPE: PRT
<213> ORGANISM: Human immunodeficiency virus type 1

<400> SEQUENCE: 1

Ser Pro Arg Thr Leu Asn Ala Trp Val Lys Val Val Glu Glu Lys Ala
1               5                   10                  15

Phe Ser Pro Glu Val Ile Pro Met Phe Ser Ala Leu Ser Glu Gly Ala
            20                  25                  30

Thr Pro Gln Asp Leu Asn Thr Met Leu Asn Thr Val Gly Gly His Gln
        35                  40                  45

Ala Ala Met Gln Met Leu Lys Glu Thr Ile Asn Glu Glu Ala Ala Glu
    50                  55                  60

Trp Asp Arg
65


<210> SEQ ID NO 2
<211> LENGTH: 67
<212> TYPE: PRT
<213> ORGANISM: Human immunodeficiency virus type 1

<400> SEQUENCE: 2

Thr Pro Arg Thr Leu Asn Ala Trp Val Lys Val Val Glu Glu Lys Ala
1               5                   10                  15
```

```
Phe Ser Pro Glu Val Ile Pro Met Phe Thr Ala Leu Ser Glu Gly Ala
            20                  25                  30

Thr Pro Ser Asp Leu Asn Thr Met Leu Asn Thr Ile Gly Gly His Gln
        35                  40                  45

Ala Ala Met Gln Met Leu Lys Asp Thr Ile Asn Glu Glu Ala Ala Glu
    50                  55                  60

Trp Asp Arg
65


<210> SEQ ID NO 3
<211> LENGTH: 67
<212> TYPE: PRT
<213> ORGANISM: Human immunodeficiency virus type 1

<400> SEQUENCE: 3

Ser Ala Arg Thr Leu Asn Ala Trp Val Lys Val Val Glu Glu Lys Gly
1               5                   10                  15

Phe Asn Pro Glu Val Ile Pro Met Phe Ser Ala Leu Ser Glu Gly Ala
            20                  25                  30

Thr Pro Gln Asp Leu Asn Thr Met Leu Asn Thr Val Gly Gly His Gln
        35                  40                  45

Ala Ala Met Gln Met Leu Lys Glu Thr Ile Asn Glu Glu Ala Ala Glu
    50                  55                  60

Trp Asp Arg
65


<210> SEQ ID NO 4
<211> LENGTH: 67
<212> TYPE: PRT
<213> ORGANISM: Human immunodeficiency virus type 1

<400> SEQUENCE: 4

Ser Pro Arg Thr Leu Asn Ala Trp Val Lys Val Ile Glu Glu Lys Ala
1               5                   10                  15

Phe Ser Pro Glu Val Ile Pro Met Phe Ser Ala Leu Ala Glu Gly Ala
            20                  25                  30

Thr Pro Gln Asp Leu Asn Met Met Leu Asn Ile Val Gly Gly His Gln
        35                  40                  45

Ala Ala Met Gln Met Leu Lys Asp Thr Ile Asn Asp Glu Ala Ala Glu
    50                  55                  60

Trp Asp Arg
65


<210> SEQ ID NO 5
<211> LENGTH: 86
<212> TYPE: PRT
<213> ORGANISM: Human immunodeficiency virus type 1

<400> SEQUENCE: 5

Asn Pro Pro Ile Pro Val Gly Glu Ile Tyr Lys Arg Trp Ile Ile Leu
1               5                   10                  15

Gly Leu Asn Lys Ile Val Arg Met Tyr Ser Pro Thr Ser Ile Leu Asp
            20                  25                  30

Ile Arg Gln Gly Pro Lys Glu Pro Phe Arg Asp Tyr Val Asp Arg Phe
        35                  40                  45

Tyr Lys Thr Leu Arg Ala Glu Gln Ala Ser Gln Glu Val Lys Asn Trp
    50                  55                  60
```

-continued

```
Met Thr Glu Thr Leu Leu Val Gln Asn Ala Asn Pro Asp Cys Lys Thr
65                  70                  75                  80

Ile Leu Lys Ala Leu Gly
                85


<210> SEQ ID NO 6
<211> LENGTH: 86
<212> TYPE: PRT
<213> ORGANISM: Human immunodeficiency virus type 1

<400> SEQUENCE: 6

Asn Pro Pro Ile Pro Val Gly Asp Ile Tyr Lys Arg Trp Ile Ile Leu
1               5                   10                  15

Gly Leu Asp Lys Ile Val Arg Met Tyr Ser Pro Thr Ser Ile Leu Asp
            20                  25                  30

Ile Arg Gln Gly Pro Lys Glu Pro Phe Arg Asp Tyr Val Asp Arg Phe
        35                  40                  45

Phe Lys Val Leu Arg Ala Glu Gln Ala Thr Gln Asp Val Lys Asn Trp
    50                  55                  60

Met Thr Asp Thr Leu Leu Val Gln Asn Ala Asn Pro Asp Cys Lys Thr
65                  70                  75                  80

Ile Leu Arg Ala Leu Gly
                85


<210> SEQ ID NO 7
<211> LENGTH: 86
<212> TYPE: PRT
<213> ORGANISM: Human immunodeficiency virus type 1

<400> SEQUENCE: 7

Asn Pro Pro Val Pro Val Gly Glu Ile Tyr Lys Arg Trp Ile Val Leu
1               5                   10                  15

Gly Leu Asn Lys Ile Val Arg Met Tyr Ser Pro Val Ser Ile Leu Asp
            20                  25                  30

Ile Arg Gln Gly Pro Lys Glu Ser Phe Arg Asp Tyr Val Asp Arg Phe
        35                  40                  45

Tyr Lys Thr Leu Arg Ala Glu Gln Ala Ser Gln Asp Val Lys Asn Trp
    50                  55                  60

Met Thr Glu Thr Leu Leu Val Gln Asn Ser Asn Pro Asp Cys Lys Thr
65                  70                  75                  80

Ile Leu Lys Ala Leu Gly
                85


<210> SEQ ID NO 8
<211> LENGTH: 86
<212> TYPE: PRT
<213> ORGANISM: Human immunodeficiency virus type 1

<400> SEQUENCE: 8

Asn Pro Pro Ile Pro Val Gly Glu Ile Tyr Lys Arg Trp Ile Ile Leu
1               5                   10                  15

Gly Leu Asn Lys Ile Val Arg Met Tyr Ser Pro Val Ser Ile Leu Asp
            20                  25                  30

Ile Lys Gln Gly Pro Lys Glu Pro Phe Arg Asp Tyr Val Asp Arg Phe
        35                  40                  45

Phe Lys Thr Leu Arg Ala Glu Gln Ala Thr Gln Glu Val Lys Asn Trp
    50                  55                  60

Met Thr Glu Thr Leu Leu Val Gln Asn Ala Asn Pro Asp Cys Lys Ser
```

65 70 75 80

Ile Leu Lys Ala Leu Gly
85

<210> SEQ ID NO 9
<211> LENGTH: 86
<212> TYPE: PRT
<213> ORGANISM: Human immunodeficiency virus type 1

<400> SEQUENCE: 9

Gly Phe Leu Gly Ala Ala Gly Ser Thr Met Gly Ala Ala Ser Met Thr
1 5 10 15

Leu Thr Val Gln Ala Arg Gln Leu Leu Ser Gly Ile Val Gln Gln Gln
20 25 30

Asn Asn Leu Leu Arg Ala Ile Glu Ala Gln Gln His Leu Leu Gln Leu
35 40 45

Thr Val Trp Gly Ile Lys Gln Leu Gln Ala Arg Val Leu Ala Val Glu
50 55 60

Arg Tyr Leu Lys Asp Gln Gln Leu Leu Gly Ile Trp Gly Cys Ser Gly
65 70 75 80

Lys Leu Ile Cys Thr Thr
85

<210> SEQ ID NO 10
<211> LENGTH: 86
<212> TYPE: PRT
<213> ORGANISM: Human immunodeficiency virus type 1

<400> SEQUENCE: 10

Gly Phe Leu Gly Val Ala Gly Ser Thr Met Gly Ala Ala Ser Ile Thr
1 5 10 15

Leu Thr Val Gln Ala Arg Gln Leu Leu Ser Gly Ile Val Gln Gln Gln
20 25 30

Ser Asn Leu Leu Arg Ala Ile Glu Ala Gln Gln His Leu Leu Lys Leu
35 40 45

Thr Val Trp Gly Ile Lys Gln Leu Gln Thr Arg Val Leu Ala Ile Glu
50 55 60

Arg Tyr Leu Lys Asp Gln Gln Leu Leu Gly Leu Trp Gly Cys Ser Gly
65 70 75 80

Lys Leu Ile Cys Pro Thr
85

<210> SEQ ID NO 11
<211> LENGTH: 86
<212> TYPE: PRT
<213> ORGANISM: Human immunodeficiency virus type 1

<400> SEQUENCE: 11

Gly Phe Leu Gly Thr Ala Gly Ser Thr Met Gly Ala Ala Ser Leu Thr
1 5 10 15

Leu Thr Val Gln Ala Arg Gln Val Leu Ser Gly Ile Val Gln Gln Gln
20 25 30

Asn Asn Leu Leu Arg Ala Ile Glu Ala Gln Gln His Met Leu Gln Leu
35 40 45

Thr Val Trp Gly Ile Lys Gln Leu Gln Ala Arg Val Leu Ala Val Glu
50 55 60

Arg Tyr Leu Lys Asp Gln Gln Leu Leu Gly Ile Trp Gly Cys Ser Gly
65 70 75 80

Lys Ile Ile Cys Thr Thr
85

<210> SEQ ID NO 12
<211> LENGTH: 86
<212> TYPE: PRT
<213> ORGANISM: Human immunodeficiency virus type 1

<400> SEQUENCE: 12

Gly Phe Leu Gly Ala Ala Gly Ser Thr Met Gly Ala Ala Ser Met Thr
1 5 10 15

Leu Thr Val Gln Ala Arg Leu Leu Leu Ser Gly Ile Val Gln Gln Gln
20 25 30

Ser Asn Leu Leu Lys Ala Ile Glu Ala Gln Gln His Leu Leu Gln Leu
35 40 45

Thr Val Trp Gly Ile Lys Gln Leu Gln Ala Arg Ile Leu Ala Val Glu
50 55 60

Arg Tyr Leu Arg Asp Gln Gln Leu Leu Gly Ile Trp Gly Cys Ser Gly
65 70 75 80

Lys Leu Ile Cys Thr Thr
85

<210> SEQ ID NO 13
<211> LENGTH: 43
<212> TYPE: PRT
<213> ORGANISM: Human immunodeficiency virus type 1

<400> SEQUENCE: 13

Arg Gln Asp Ile Leu Asp Leu Trp Val Tyr His Thr Gln Gly Tyr Phe
1 5 10 15

Pro Asp Trp Gln Asn Tyr Thr Pro Gly Pro Gly Ile Arg Tyr Pro Leu
20 25 30

Thr Phe Gly Trp Cys Phe Lys Leu Val Pro Val
35 40

<210> SEQ ID NO 14
<211> LENGTH: 43
<212> TYPE: PRT
<213> ORGANISM: Human immunodeficiency virus type 1

<400> SEQUENCE: 14

Arg Gln Glu Ile Leu Asp Leu Trp Val Tyr His Thr Gln Gly Phe Phe
1 5 10 15

Pro Asp Trp Gln Asn Tyr Thr Pro Gly Pro Gly Ile Arg Tyr Pro Leu
20 25 30

Thr Phe Gly Trp Cys Tyr Lys Leu Val Pro Val
35 40

<210> SEQ ID NO 15
<211> LENGTH: 43
<212> TYPE: PRT
<213> ORGANISM: Human immunodeficiency virus type 1

<400> SEQUENCE: 15

Arg Lys Asp Ile Leu Asp Leu Trp Val Tyr Asn Thr Gln Gly Tyr Phe
1 5 10 15

Pro Asp Trp His Asn Tyr Thr Pro Gly Pro Gly Thr Arg Phe Pro Leu
20 25 30

Thr Phe Gly Trp Cys Phe Lys Leu Val Pro Val

-continued

```
        35                  40


<210> SEQ ID NO 16
<211> LENGTH: 43
<212> TYPE: PRT
<213> ORGANISM: Human immunodeficiency virus type 1

<400> SEQUENCE: 16

Arg Gln Asp Ile Leu Asp Leu Trp Val Tyr His Thr Gln Gly Tyr Phe
1               5                   10                  15

Pro Asp Trp Gln Asn Tyr Thr Pro Gly Pro Gly Val Arg Tyr Pro Leu
            20                  25                  30

Thr Phe Gly Trp Cys Phe Glu Leu Val Pro Val
        35                  40


<210> SEQ ID NO 17
<211> LENGTH: 15
<212> TYPE: PRT
<213> ORGANISM: Artificial Sequence
<220> FEATURE:
<223> OTHER INFORMATION: Synthetic flexible linker

<400> SEQUENCE: 17

Gly Gly Gly Gly Ser Gly Gly Gly Gly Ser Gly Gly Gly Gly Ser
1               5                   10                  15
```